United States Patent [19]
Yokoyama et al.

[11] Patent Number: 5,707,417
[45] Date of Patent: Jan. 13, 1998

[54] PROCESS OF TREATING GARBAGE WITH SIMULTANEOUS PRODUCTION OF METHANE

[75] Inventors: Shinya Yokoyama; Tomoko Ogi; Shigeki Sawayama; Tomoaki Minowa; Seiichi Inoue, all of Tsukuba, Japan

[73] Assignee: Director-General of Agency of Industrial Science and Technology, Japan

[21] Appl. No.: 506,192

[22] Filed: Jul. 24, 1995

[30] Foreign Application Priority Data

Sep. 30, 1994 [JP] Japan .................................. 6-236643

[51] Int. Cl.$^6$ ...................................................... C05F 9/04
[52] U.S. Cl. .......................... 71/10; 71/14; 71/15; 71/901
[58] Field of Search ................................. 71/1, 11, 15, 23, 71/8–10, 901, 14

[56] References Cited

U.S. PATENT DOCUMENTS 3,953,191  4/1976  Barton .......................................... 71/23

*Primary Examiner*—Ferris Lander
*Attorney, Agent, or Firm*—Lorusso & Loud

[57] ABSTRACT

Garbage resulting from the preparation, cooking and dispensing of food and containing water-insoluble organic components is treated first heated in the presence of water at a temperature of 100°–400° C. and a pressure higher than the saturated water vapor pressure to convert at least part of the water-insoluble components into water-soluble organic components and to obtain a mixture containing the water-soluble components dissolved in the water. The mixture is then subjected to methane fermentation to convert the water-soluble organic components into methane.

20 Claims, 1 Drawing Sheet

PROCESS OF TREATING GARBAGE WITH SIMULTANEOUS PRODUCTION OF METHANE

BACKGROUND OF THE INVENTION

This invention relates generally to a process of treating garbage and, more particularly, to a process of treating garbage with the simultaneous production of methane.

A huge amount of garbage, resulting from the preparation, cooking and dispensing of food, is discharged from homes, restaurants, food shops, manufactories, etc. Hitherto, such refuse has been collected and either burned with an auxiliary fuel or used for land reclamation. The conventional treatment methods, however, cause a problem of environmental pollution and consumption of energy. It is known to anaerobically digest garbage to produce methane or to convert garbage to form compost. These methods have a problem because a long period of time (more than about 1 month) is required for the completion of the treatment.

SUMMARY OF THE INVENTION

It is, therefore, an object of the present invention to provide a process of treating garbage which requires much less energy as compared with the conventional incineration method.

Another object of the present invention is to provide a process of the above-mentioned type which can yield methane.

It is a further object of the present invention to provide a process of the above-mentioned type which can produce, in addition to methane, solids which may be easily combusted as such or may be processed into compost.

In accomplishing the foregoing objects, the present invention provides a process of treating garbage resulting from the preparation, cooking and dispensing of food and containing water-insoluble organic components, which includes the steps of:

(a) heating the garbage in the presence of water at a temperature of 100°–400° C. and a pressure higher than the saturated water vapor pressure to convert at least part of the water-insoluble components into water-soluble organic components and to obtain a mixture containing the water-soluble components dissolved in the water, and (b) subjecting the mixture to methane fermentation to convert the water-soluble organic components into methane.

Before step (b), the mixture may be separated into a solid phase and a liquid phase containing the water-soluble organic components, the liquid phase being subjected to the methane fermentation. The solid phase may be burnt as such without a fuel or may be converted into compost.

BRIEF DESCRIPTION OF THE DRAWING

Other objects, features and advantages of the present invention will become apparent from the detailed description of the invention which follows, when considered in light of the accompanying drawing, in which:

the sole FIGURE is a flow diagram schematically showing an apparatus for carrying out the process of the present invention.

DETAILED DESCRIPTION OF THE PREFERRED EMBODIMENTS OF THE INVENTION

Figure 1:
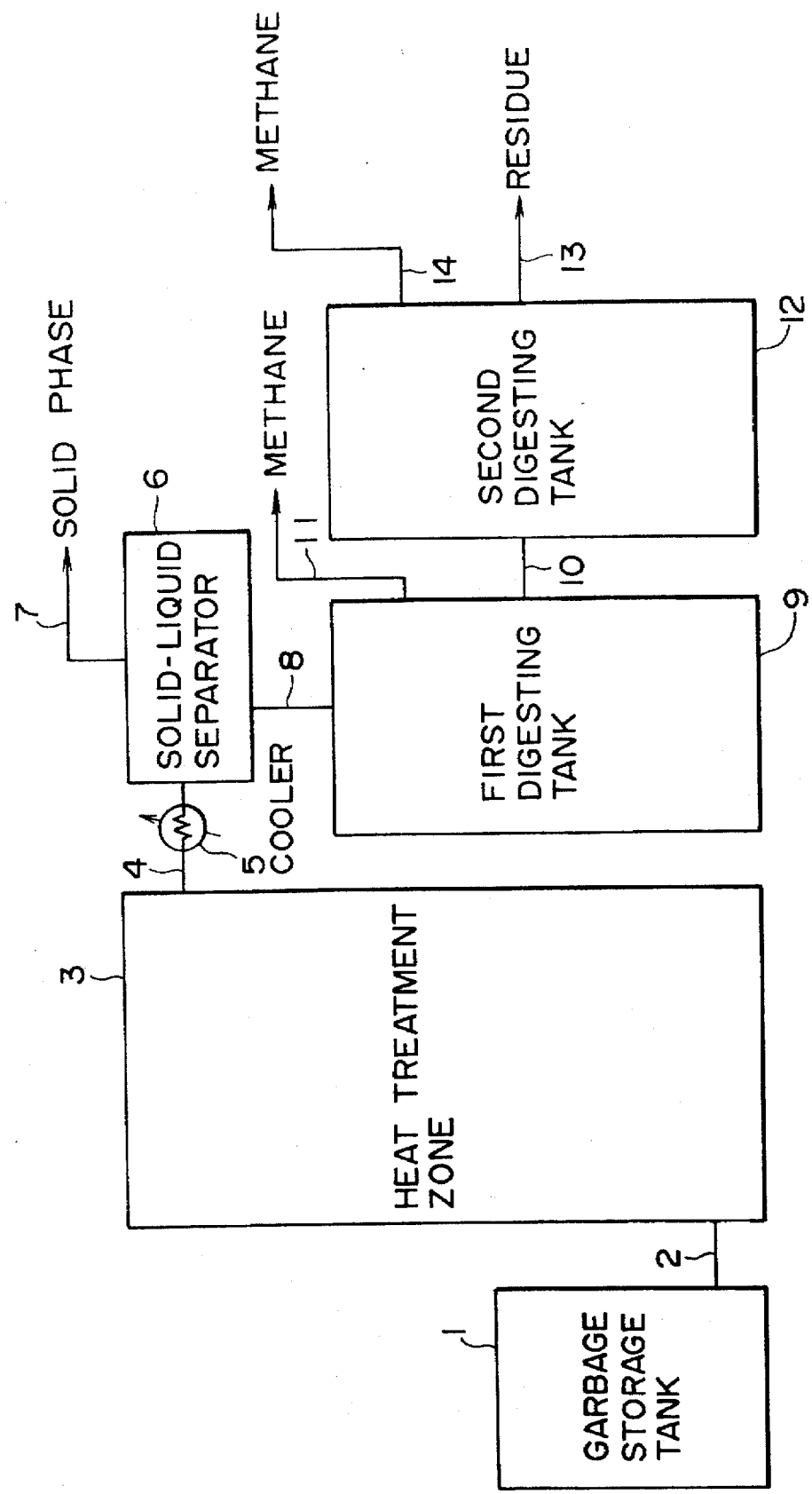

Garbage to be treated in the present invention generally contains water in an amount of 50–99% by weight and as such may be used for the purpose of the present invention. A condensed mass obtained by dehydrating or drying garbage may also be treated according to the present invention.

The garbage is heated at a temperature of 100°–400° C., preferably 150°–200° C. and a pressure higher than the saturated water vapor pressure to convert at least part of the water-insoluble components into water-soluble organic components and to obtain a mixture containing the water-soluble components dissolved in the water. The treatment pressure is preferably 2–200 atm, more preferably 5–50 atm, while the treatment time is generally 1–720 minutes, preferably 30–90 minutes. If desired, an oxygen-free gas such as nitrogen, argon, helium or carbon dioxide may be used to maintain the desired treatment pressure. In such a case, the heat treatment zone containing the garbage is pressurized at 2–50 atm with the oxygen-free gas before heating to the treatment temperature.

Through the heat treatment, the walls and membranes of the cells constituting the garbage are destroyed so that the garbage is liquidized (or fluidized). Simultaneously, part of high molecular weight organic substances are converted into low molecular weight compounds. When the garbage-liquidization treatment is performed excessively, conversion of the organic components into an oil significantly takes place. Oil production is undesirable for the purpose of the present invention because the methane yield is lowered. Thus, it is preferred that the heat treatment be continued until 30–80% by weight, more preferably 50–60% by weight, of the organic materials is dissolved in the water. The organic materials contained in the heat-treated, liquidized garbage preferably have a carbon content of 20–80% by weight, more preferably 40–60% by weight, a hydrogen content of 2–15% by weight, more preferably 5–7% by weight, and an oxygen content of 10–70% by weight, more preferably 30–50% by weight, by elemental analysis.

In the present specification, the total organic material content in the liquidized garbage is as measured by the following method:

The heat treated product is dried at 105° C. for 24 hours. The dried mass is then heated at 600° C. for 1 hour to burn the combustible materials contained therein and to leave a combustion residue. The organic material content Wo is given by Wo=Wd−Wb wherein Wd and Wb represent the weight of the dried mass and the weight of the combustion residue, respectively.

The amount of the organic materials dissolved in the water by the heat treatment is measured as follows:

The heat treated product is filtered with a nylon filter (mesh size: 20 μm). The filtrate is dried and burned in the same manner as described above and the organic material content is calculated as described above.

The heat treated, liquidized product is then subjected to a methane fermentation treatment (anaerobic digestion). The methane fermentation treatment per se is well known in the art and may be carried out in any known manner, such as by a contact process, a process using an anaerobic filter, a process using a fluidized bed system or a process using an upflow anaerobic sludge blanket (UASB) reactor, using methane bacteria. The methane fermentation is generally performed so that the organic material is loaded on a methane bacteria culture liquid in an amount of 0.1–100 g per liter of the culture liquid per day (g/L/day), preferably 2–8 g/L/day. The methane gas produced by the fermentation treatment is recovered and is utilized as a fuel or a raw material.

In one preferred embodiment, the heat treated, liquidized product is first separated into a liquid phase and a solid phase and the liquid phase is then subjected to the methane fermentation treatment. Any solid-liquid separation technique, such as centrifugation, sedimentation, belt press separation or filtration, may be suitably used for the purpose of the present invention. Since the garbage has been heat-treated, the liquidized product and the separated products thereof can be handled in a hygienically acceptable condition.

The liquid phase generally contains at least 2% by weight, typically 4–10% by weight, of water soluble organic materials and is very suited for methane fermentation. The solid phase generally contains at least 20% by weight, typically 20–40% by weight, of organic materials and may be combusted as such or after drying without using an auxiliary fuel. Alternatively, the solid phase may be converted into compost by fermentation in any known manner.

One preferred embodiment of an apparatus for carrying out the above process is shown in FIGURE. Designated as 1 is a storage tank in which garbage to be treated is stored. The garbage is fed through a line 2 to a heat treatment zone 3 which is composed of an outer cylinder and an inner cylinder disposed within the outer cylinder to form an annular space therebetween. The garbage feed is introduced into the inner cylinder and is displaced upward therethrough by pumping pressure. During the passage through the inner cylinder, the garbage feed is heated with a heating medium supplied to the annular space, so that the garbage is heat treated under an autogeneous pressure.

The heat-treated, liquidized product is discharged from the heat treatment zone 3 through a line 4, cooled to below 100° C. in a cooler 5 and is introduced into a solid-liquid separator 6, where the product is separated into a solid phase and a liquid phase. The solid phase is discharged from the separator 6 through a line 7 and is recovered, while the liquid phase is discharged from the separator through a line 8 and is fed to a first digesting tank 9. In the tank 9, the liquid phase is anaerobically digested with methane bacteria to produce methane which is withdrawn overhead from the tank 9 through a line 11. The digestion residue is fed through a line 10 to a second digesting tank 12 and subjected to anaerobic digestion. The methane gas produced is withdrawn from the tank 12 through a line 14, while the digestion residue, generally including inorganic substances such as metals and phosphates and organic substances such as keratin and humic acid which are hard to decompose, is discharged through a line 13.

The following examples will further illustrate the present invention. Parts and percentages are by weight.

EXAMPLE 1

Garbage composed of 320.4 parts of cabbage, 18.4 parts of boiled rice, 2.0 parts of dried small sardines, 2.1 parts of butter and 3.9 parts of shells and having a water content of 88.7% and an organic material content of 10.2% was treated according to the process of the present invention. Thus, 347 g of the garbage were placed in a stainless steel autoclave (inside volume: 1 liter) and heated at about 175° C. under an autogeneous pressure for 1 hour. The pressure within the autoclave at that temperature was about 40 atm.

The heat-treated, liquidized product was cooled to room temperature. This liquidized product was found to have a water content of 90.9%, a total organic material content of 8.2% and a water soluble organic material content of 4.6%. To a methane bacteria culture liquid (2 liters, bacteria content: about 1.1%) incubated at 35° C., 49 g (total organic material: 4.0 g) of the liquidized product were added (the organic material load was thus 2.0 g/liter) and the resulting mixture was then incubated at 35° C. to effect methane fermentation for 6 days. The gas generated during the fermentation was measured by gas chromatography for the amount of methane produced. The cumulative amount of total gas produced and cumulative amount of methane produced each per gram of the total organic material subjected to the methane fermentation are shown in Table 1.

TABLE 1

| Fermentation Period (day) | Cumulative Amount of Total Gas (ml/g) | Cumulative Amount of Methane (ml/g) |
| --- | --- | --- |
| 1 | 148 | 85 |
| 2 | 215 | 126 |
| 3 | 239 | 142 |
| 4 | 263 | 158 |
| 5 | 263 | 158 |
| 6 | 263 | 158 |

The methane fermentation was completed after 4 days. About 60% of the total organic material was decomposed through the 4 day fermentation.

EXAMPLE 2

The heat-treated, liquidized product obtained in Example 1 was separated by filtration with a nylon filter (mesh size: 20 μm) into 87.2% of a liquid phase having a water content of 93.9% and an organic material content of 5.4% and 12.8% of a solid phase having a water content of 69.9% and an organic material content of 29.2%.

The liquid phase was mixed with a methane bacteria culture liquid (2 liters) in such an amount as to provide an organic material load of 1.8 g/liter and the resulting mixture was then incubated at 35° C. to effect methane fermentation for 6 days in the same manner as that in Example 1. The results are summarized in Table 2.

TABLE 2

| Fermentation Period (day) | Cumulative Amount of Total Gas (ml/g) | Cumulative Amount of Methane (ml/g) |
| --- | --- | --- |
| 1 | 194 | 114 |
| 2 | 266 | 154 |
| 3 | 315 | 178 |
| 4 | 354 | 193 |
| 5 | 354 | 193 |
| 6 | 354 | 193 |

The methane fermentation was completed after 4 days. About 70% of the total organic material was decomposed through the 4 day fermentation.

The elemental analysis of the solid phase obtained by the filtration gave:

C: 59.6% H: 6.65% O: 29.0%.

The solid phase was self-combustible and had a higher calorific value of 1,720 kcal/kg and a lower calorific value of 942 kcal/kg when calculated according to the Dulong's equation.

Comparative Example 1

The garbage shown in Example 1 was mixed with an equal amount of water and the mixture was pulverized with a mixer. The resulting slurry was mixed with a methane bacteria culture liquid (2 liters) in such an amount as to provide an organic material load of 2.0 g/liter and the resulting mixture was then incubated at 35° C. to effect methane fermentation for 6 days in the same manner as that in Example 1. The results are summarized in Table 3.

TABLE 3

| Fermentation Period (day) | Cumulative Amount of Total Gas (ml/g) | Cumulative Amount of Methane (ml/g) |
|---|---|---|
| 1 | 66 | 13 |
| 2 | 101 | 22 |
| 3 | 117 | 28 |
| 4 | 119 | 29 |
| 5 | 127 | 32 |
| 6 | 132 | 34 |

About 54% of the total organic material was decomposed through the 4 day fermentation.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A process of treating garbage resulting from the preparation, cooking and dispensing of food and containing water-insoluble organic components, comprising the steps of:
   (a) heating said garbage in the presence of water at a temperature of 100°–400° C. and a pressure higher than the saturated water vapor pressure to convert at least part of said water-insoluble components into water-soluble organic components and to obtain a mixture containing said water-soluble components dissolved in said water, and
   (b) subjecting said mixture to methane fermentation to convert said water-soluble organic components into methane.

2. A process as set forth in claim 1, wherein, before step (b), said mixture is separated into a solid phase and a liquid phase containing said water-soluble organic components, said liquid phase being subjected to said methane fermentation.

3. A process as set forth in claim 2 wherein said heating is continued until 30–80% of the water-insoluble organic components are converted into the water-soluble organic components and are dissolved in said water.

4. A process as set forth in claim 3 wherein said pressure is 2–200 atmospheres.

5. A process as set forth in claim 4 wherein said heating is in an atmosphere devoid of free oxygen gas.

6. A process as set forth in claim 5 wherein said atmosphere is nitrogen, argon, helium or carbon dioxide.

7. A process as set forth in claim 2, further comprising recovering and burning said solid phase.

8. A process as set forth in claim 2, further comprising recovering said solid phase and processing said recovered solid phase into a compost.

9. A process as set forth in claim 1, further comprising recovering said methane.

10. A process as set forth in claim 2, further comprising recovering said methane.

11. A process as set forth in claim 1 wherein said pressure is 2–200 atmospheres.

12. A process as set forth in claim 11 wherein said heating is continued until 30–80% of the water-insoluble organic components are converted into the water-soluble organic components and are dissolved in said water.

13. A process as set forth in claim 11 wherein said heating is in an atmosphere devoid of free oxygen gas.

14. A process as set forth in claim 13 wherein said atmosphere is nitrogen, argon, helium or carbon dioxide.

15. A process as set forth in claim 1 wherein said pressure is 5–50 atmospheres.

16. A process as set forth in claim 1 wherein said heating is conducted for 1–720 minutes.

17. A process as set forth in claim 1 wherein said heating is conducted for 30–90 minutes.

18. A process as set forth in claim 1 wherein said heating is in an atmosphere devoid of free oxygen gas.

19. A process as set forth in claim 18 wherein said atmosphere is nitrogen, argon, helium or carbon dioxide.

20. A process as set forth in claim 1 wherein said heating is continued until 30–80% of the water-insoluble organic components are converted into the water-soluble organic components and are dissolved in said water.

* * * * *